(12) United States Patent
Begg

(10) Patent No.: US 11,058,812 B2
(45) Date of Patent: Jul. 13, 2021

(54) INTRAVENOUS BAG ATTACHMENT

(71) Applicant: Lydia Begg, Parrish, FL (US)

(72) Inventor: Lydia Begg, Parrish, FL (US)

(*) Notice: Subject to any disclaimer, the term of this patent is extended or adjusted under 35 U.S.C. 154(b) by 325 days.

(21) Appl. No.: 16/044,599

(22) Filed: Jul. 25, 2018

(65) Prior Publication Data

US 2019/0030237 A1    Jan. 31, 2019

Related U.S. Application Data

(60) Provisional application No. 62/536,652, filed on Jul. 25, 2017.

(51) Int. Cl.
| | |
|---|---|
| *A61M 5/14* | (2006.01) |
| *A61J 1/14* | (2006.01) |
| *A61M 39/08* | (2006.01) |
| *A61J 1/10* | (2006.01) |

(52) U.S. Cl.
CPC ............ *A61M 5/14* (2013.01); *A61J 1/14* (2013.01); *A61M 39/08* (2013.01); *A61J 1/10* (2013.01); *A61M 2005/1403* (2013.01)

(58) Field of Classification Search
CPC ............ A61M 5/14; A61M 39/08; A61M 2005/1403; A61M 39/20; A61M 5/40; A61J 1/10; A61J 1/14; A61F 5/4405; F16K 21/18; F16K 31/18
See application file for complete search history.

(56) References Cited

U.S. PATENT DOCUMENTS

| | | | |
|---|---|---|---|
| 4,267,834 A | 5/1981 | Barger et al. | |
| 5,242,392 A | 9/1993 | Vaughn | |
| 5,308,334 A | 5/1994 | Sancoff | |
| 6,391,001 B1 | 5/2002 | Graham et al. | |
| 8,430,859 B2 | 4/2013 | McConnell | |
| 2014/0303568 A1 | 10/2014 | Wiest et al. | |

FOREIGN PATENT DOCUMENTS

WO    WO-0040283 A1 *    7/2000    ............ A61M 5/40

* cited by examiner

*Primary Examiner* — Laura A Bouchelle
*Assistant Examiner* — Courtney B Fredrickson
(74) *Attorney, Agent, or Firm* — Boudwin Intellectual Property; Daniel Boudwin

(57) ABSTRACT

An intravenous bag attachment for automatically flushing remnants out from an intravenous line after the contents of a connected intravenous bag have emptied out. The attachment includes a container having a tubular member in fluid communication with an interior volume designed to hold a flushing solution. The tubular member is designed to create an opening and be inserted into an intravenous bag, and to act as a float valve that will remain closed while the amount of liquid remaining in the intravenous bag is above a predefined threshold, and that will open once the amount of liquid remaining in the intravenous bag falls below the predefined threshold. The float valve further includes a ball float designed to keep the tubular member upright, such that the float valve is closed, and to allow the flushing solution to exit through the tubular member when the float valve is open.

9 Claims, 3 Drawing Sheets

INTRAVENOUS BAG ATTACHMENT

CROSS REFERENCE TO RELATED APPLICATION

This application claims the benefit of U.S. Provisional Application No. 62/536,652 filed on Jul. 25, 2017. The above identified patent application is herein incorporated by reference in its entirety to provide continuity of disclosure.

BACKGROUND OF THE INVENTION

The present invention relates to the cleaning of intravenous tubes. More specifically, the present invention provides an attachment for intravenous bags that automatically releases a flushing solution in the amount of 20-25 ml post intravenous medication infusion to ensure that patients to receive a full dosage of intravenous medication and that no medication is left over and wasted in the tubing.

The flushing solution in the attachment has to be the same composition as the mixing solution of the infused medication. The solution in the attachment has to be free of any medication to ensure compatibility. For example, if the intravenous antibiotic is mixed in a bag with Sodium Chloride 0.9%, then the attachment should contain Sodium Chloride 0.9%, or if the antibiotic is mixed in a bag with Dextrose 5% water, then the attachment should contain Dextrose 5% water. Ultimately, the intravenous bags and the attachments should contain the same basic solution.

Every year millions of dollars are spent on expensive intravenous antibiotics and prolonged hospital stays. The purpose of this attachment is to stop wasting costly medication and to prevent delays in treatment. Furthermore, not only is part of the medication left in the tubing, but air is also left within the intravenous tubing set from the previous dose of medication, and this air could be lethal to the patient.

Frequently, many medical professionals switch back and forth between multiple secondary intravenous tubes when medicating patients, which breaks the closed system of delivering medicine intravenously and thereby increases the risk of infection. Currently, many hospitals employ a closed system wherein a secondary intravenous bag is hooked to a primary intravenous larger bag that is supposed to be continuously infused and can last 96 hours before exchange. This closed system is frequently broken and causes patients to become compromised with blood infection. Additionally, many of the compromised patients are suffering from heart or renal failure, so it is contraindicated for them to receive continuous infusions. In fact, any incidence of intravenous bags being changed, or where patients are otherwise unhooked and re-hooked to an intravenous bag, also breaks the closed system and increases the possibility of infection.

If patients lose 10-15 ml out of 100 ml intravenous bags with each dose, it accumulates substantial loss of necessary antibiotic treatments. The usual antibiotic treatment is prescribed to last 10 days, and the usual schedule varies from dosing every 6, 8, or 12 hours. This makes up to 40 doses in 10 days. If the patient loses 10-15% of the medication with each dose, the recovery will be delayed. As such, the attachment can dramatically reduce waste as the post flush from the attachment into the tubing will allow for complete infusion. The intravenous set is to be changed every 24 hours in this case.

Furthermore, traditional intravenous tubing is designed to last 96 hours, while intravenous bags are designed to be changed every 24 hours. The disparity in change cycles between intravenous tubes and intravenous bags occasionally leads to bags being changed before the medicinal contents have been completely used up, which is wasteful and costly.

Therefore, a device capable of automatically flushing intravenous tubes is needed. The present invention provides a means of automatically flushing intravenous tubes without breaking the closed system of delivering medicine intravenously.

Devices have been disclosed in the known art that relate to cleaning intravenous tubes. These include devices that have been patented and published in patent application publications. These devices generally relate to tubing sets having accompanying bags containing a flushing solution. However, none of these devices include a tubular member configured to be inserted into an intravenous bag in active use and to automatically deliver a flushing solution when the intravenous bag empties out.

In light of the devices disclosed in the known art, it is submitted that the present invention substantially diverges in design elements from the known art and consequently it is clear that there is a need in the art for an improvement to existing intravenous bag attachment devices. In this regard the instant invention substantially fulfills these needs.

SUMMARY OF THE INVENTION

In view of the foregoing disadvantages inherent in the known types of intravenous bag attachments now present in the known art, the present invention provides a new intravenous bag attachment wherein the same can be utilized for providing convenience for the user when administering medication intravenously.

It is therefore an object of the present invention to provide a new and improved intravenous bag attachment device that has all of the advantages of the known art and none of the disadvantages.

Another object of the present invention is to provide a container having a tubular member in fluid communication with an interior volume, such that the interior volume is configured to hold a flushing solution adapted to flush an intravenous tube.

Yet another object of the present invention is to provide a tubular member configured to be inserted into an intravenous bag, such that a distal end of the tubular member can be inserted into a proximal end of the intravenous tube.

A further object of the present invention is to provide a distal end of a tubular member configured to act as a float valve that will remain closed while the amount of liquid remaining in the intravenous bag is above a predefined threshold, and that will open once the amount of liquid remaining in the intravenous bag falls below the predefined threshold.

Another object of the present invention is to provide a float valve comprising a ball float disposed in the tubular member configured to float the distal end of the tubular member within the liquid contents of the intravenous bag, and an outlet disposed on the distal end of the tubular member configured to allow the flushing solution housed in the interior volume to exit through the tubular member and flush out the intravenous tube.

An additional object of the present invention is to provide a tubular member including a flexible joint configured to bend the distal end of the tubular member upward due to the buoyant force of the ball float when the amount of liquid remaining in the intravenous bag is above the predefined threshold, and to bend the distal end of the tubular member downward under the weight of the ball float when the mount of liquid remaining in the intravenous bag is below the predefined threshold.

Still another object of the present invention is to provide a tubular member whose distal end is configured to create an opening the intravenous bag and to facilitate fluid communication between the intravenous bag and the intravenous bag attachment.

A further object of the present invention is to provide a flexible joint on the tubular member configured to insert the distal end of the tubular member into a proximal end of the intravenous tube when the amount of liquid remaining in the intravenous bag falls below the threshold.

Another object of the present invention is to provide an intravenous bag attachment, wherein the container is a pouch.

Yet another object of the present invention is to provide an intravenous bag attachment, wherein the container is in the shape of a vertical semi-circle having a highest point, a center point, and a lowest point.

A further object of the present invention is to provide an intravenous bag attachment, wherein the tubular member is disposed along the non-circular portion of the container between the center point and the lowest point, such that the entirety of the flushing solution housed in the internal volume can automatically flow out through the tubular member under the influence of gravity alone.

Another object of the present invention is to provide an intravenous bag attachment, wherein the non-circular portion is flush against an outer surface of the intravenous bag when the tubular member is fully inserted.

Yet another object of the present invention is to provide a tubular member configured to be inserted into an attached intravenous bag on the whichever side an access port for an intravenous line is installed.

An additional object of the present invention is to provide an intravenous bag attachment, wherein the container and tubular member are both comprised of materials that are commercially and/or pharmaceutically acceptable, such as polyvinyl chloride.

Still another object of the present invention is to provide an intravenous bag attachment, wherein the ball float is comprised of a buoyant, sterile lightweight material that does not disintegrate in a fluid and is an accepted pharmaceutical material.

Another object of the present invention is to provide an intravenous bag attachment that may be readily fabricated from materials that permit relative economy and are commensurate with durability.

Other objects, features and advantages of the present invention will become apparent from the following detailed description taken in conjunction with the accompanying drawings.

BRIEF DESCRIPTIONS OF THE DRAWINGS

Although the characteristic features of this invention will be particularly pointed out in the claims, the invention itself and manner in which it may be made and used may be better understood after a review of the following description, taken in connection with the accompanying drawings wherein like numeral annotations are provided throughout.

DETAILED DESCRIPTION OF THE INVENTION

Figure 1A:
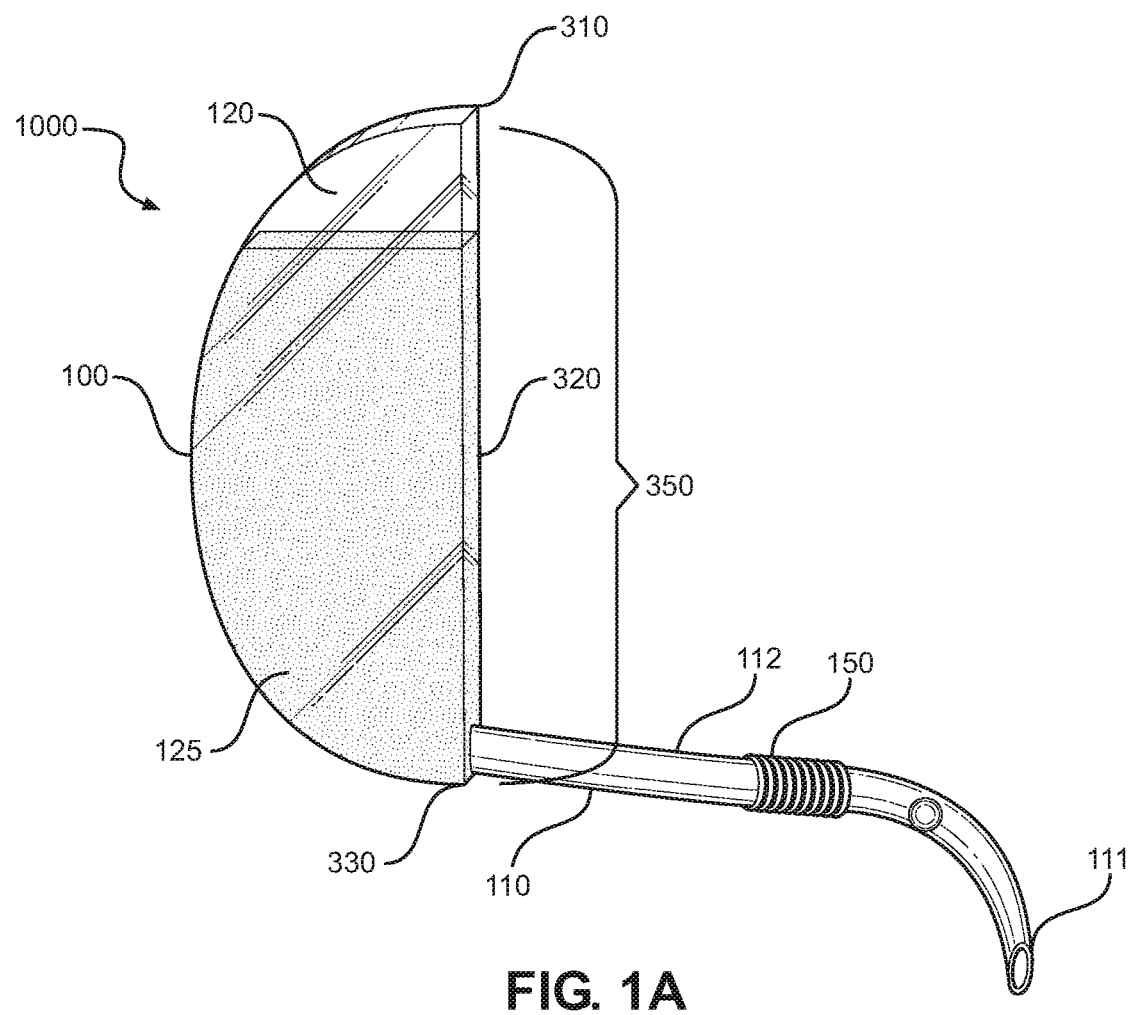
FIG. 1A shows a perspective view of an embodiment of an intravenous bag attachment.

Reference is made herein to the attached drawings. Like reference numerals are used throughout the drawings to depict like or similar elements of the intravenous bag attachment. For the purposes of presenting a brief and clear description of the present invention, the preferred embodiment will be discussed as used for intravenous bag attachments. The figures are intended for representative purposes only and should not be considered to be limiting in any respect.

Figure 1B:
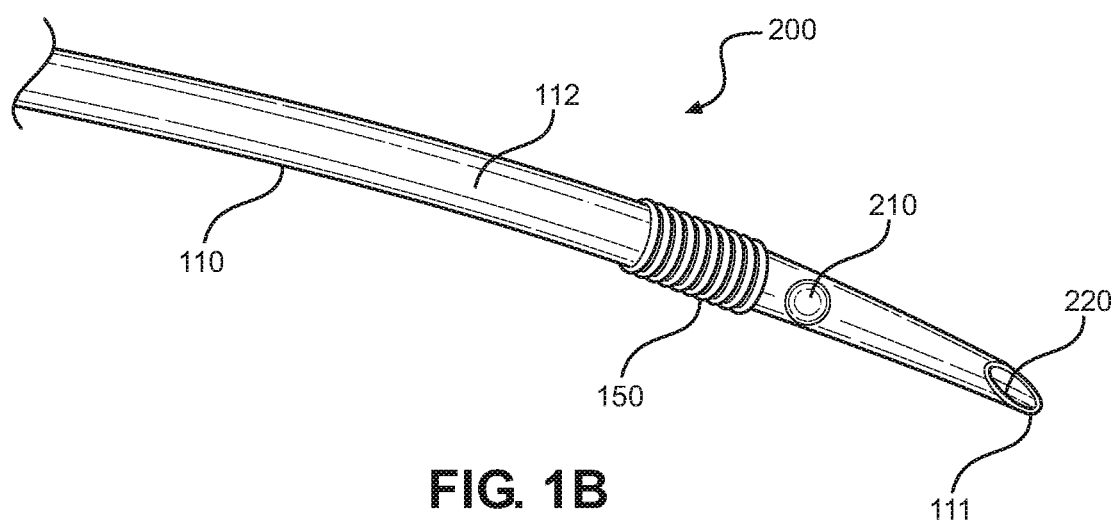
FIG. 1B shows a close-up view of a tubular member used as a float valve in an embodiment of an intravenous bag attachment.

Referring now to FIGS. 1A and 1B, there are shown a perspective view of an embodiment of an intravenous bag attachment, and a close-up view of a tubular member used as a float valve in an embodiment of an intravenous bag attachment, respectively. In the illustrated embodiment an intravenous bag attachment 1000, includes a container 100 having a tubular member 110 in fluid communication with an interior volume 120. The interior volume 120 is configured to hold a flushing solution 125 adapted to flush an intravenous tube and the tubular member 110 is configured to be inserted into an intravenous bag, such that a distal end 111 of the tubular member 110 can be inserted into a proximal end of the intravenous tube.

In one embodiment of the intravenous bag attachment, the container 100 is simply a pouch in the shape of a vertical semi-circle having a high point 310, a center point 320, and a low point 330. The tubular member 110 is disposed along a non-circular portion 350 of the container 100 between the center point 320 and the low point 330, such that the entirety of the flushing solution 125 housed in the internal volume 120 can automatically flow out through the tubular member 110 under the influence of gravity alone. Positioning the tubular member 110 lower down along the non-circular portion 350 maximizes the amount of flushing solution 125 housed in the container 100 available to flush out the intravenous tube. In the illustrated embodiment the container 100 and tubular member 110 are both comprised of polyvinyl chloride, which is the one of the materials most commonly used to manufacture intravenous bags and intravenous tubing. In other embodiments the container 100 and tubular member 110 can be comprised of any material that is commercially and/or pharmaceutically acceptable.

In FIG. 1B the distal end 111 of the tubular member 110 is further configured to act as a float valve 200 that will remain closed while the amount of liquid remaining in the intravenous bag is above a predefined threshold, and that will open once the amount of liquid remaining in the intravenous bag falls below the predefined threshold. The float valve 200 comprises a ball float 210 disposed in the tubular member 110 configured to float the distal end 111 of the tubular member 110 within the liquid contents of the intravenous bag, and an outlet 220 disposed on the distal end 111 of the tubular member 110 configured to allow the flushing solution 125 housed in the interior volume 120 to exit through the tubular member 110 and flush out the intravenous tube. In the illustrated embodiment the ball float 210 is comprised of a buoyant, sterile lightweight material that does not disintegrate in a fluid and is an accepted pharmaceutical material.

In some embodiments of the intravenous bag attachment, a flexible joint 150 is included towards the distal end 111 of the tubular member 110. The flexible joint 150 is positioned between the distal end 111 and the midway point 112 of the tubular member 110 to better facilitate the bending motion of the tubular member in its capacity as float valve 200. The flexible joint 150 is configured to point the distal end 111 of the tubular member 110 upward into a closed position, wherein the float valve 200 does not allow the flushing solution to flow through the outlet 220. The ball float 210 is configured to produce an upward buoyant force when the amount of liquid remaining in the intravenous bag is above the predefined threshold. Additionally, the flexible joint 150 is configured to point the distal end 111 of the tubular member 110 downward into an open position, wherein the float valve 200 allows the flushing solution to flow through the outlet 220. When the amount of liquid remaining in the intravenous bag is below the predefined threshold, the weight of the ball float 210 produces a force that bends the distal end 111 of the tubular member 110 downward.

Figure 2A:
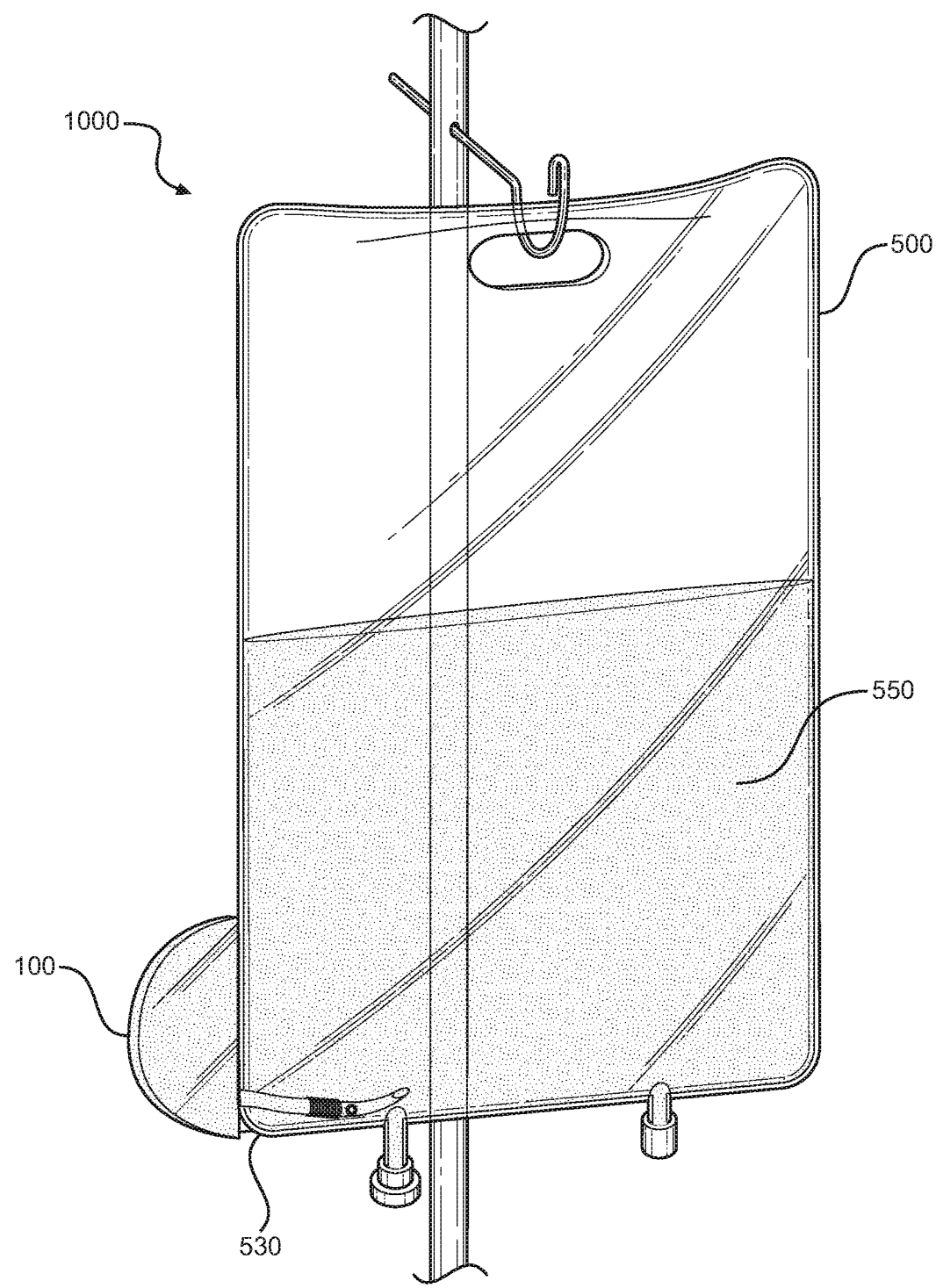
FIG. 2A shows a perspective view of an embodiment of an intravenous bag attachment in use connected to an intravenous bag.
Figure 2B:
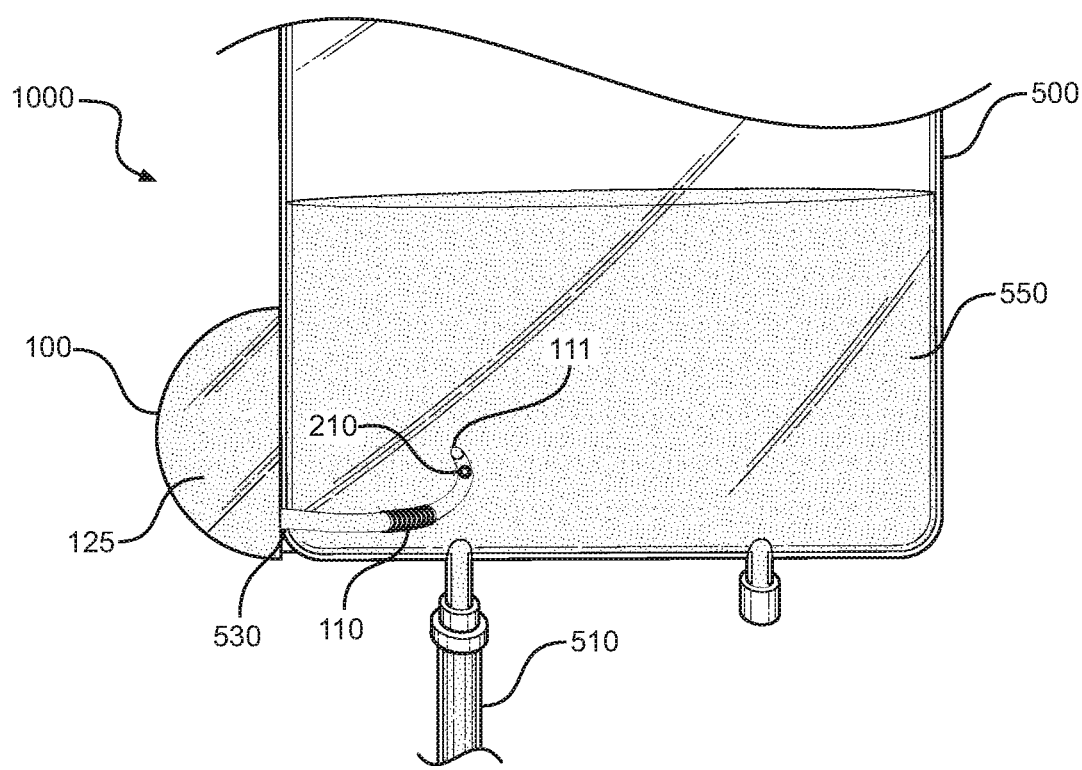
FIG. 2B shows a perspective view of an embodiment of an intravenous bag attachment in use connected to an intravenous bag, wherein the float valve is in the closed position.
Figure 2C:
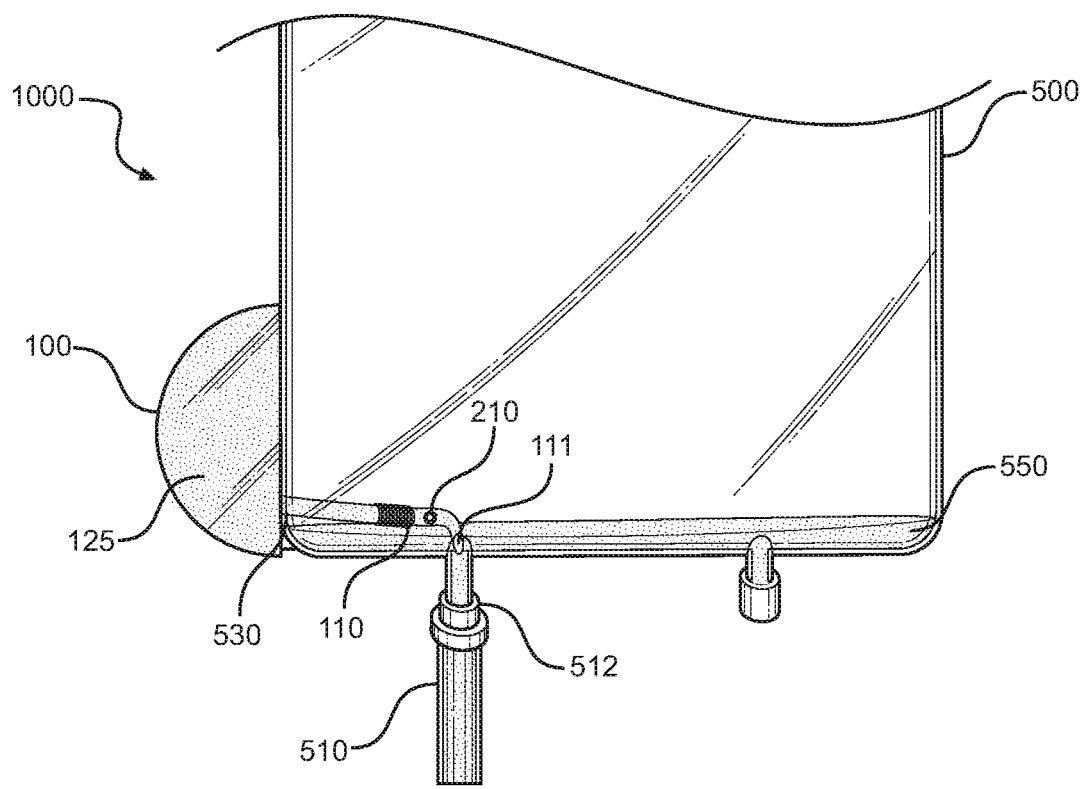
FIG. 2C shows a perspective view of an embodiment of an intravenous bag attachment in use connected to an intravenous bag, wherein the float valve is in the open position.

Referring now to FIGS. 2A, 2B, and 2C, there are shown perspective views of an embodiment of an intravenous bag attachment in use connected to an intravenous bag, wherein the float valve is in the closed position, and wherein the float valve is in the open position, respectively. In the illustrated embodiment the distal end 111 of the tubular member 110 tapers inward to a point configured to create an opening in the intravenous bag 500 thereby facilitating fluid communication between the intravenous bag 500 and the attachment 1000, and preventing the ball float 210 from escaping the tubular member 110. FIG. 2B shows the distal end 111 of the tubular member 110 pointing upward in the closed position due to the buoyant force of the ball float 210, because the amount of liquid remaining 550 in intravenous bag 500 is above the predefined threshold. FIG. 2C shows the distal end 111 of the tubular member 110 pointing downward in the open position due to the weight of the ball float and when the amount of liquid remaining 550 in the intravenous bag 500 is below the predefined threshold.

In some embodiments the tubular member 110 is configured to be inserted through a left lower portion 530 of the intravenous bag 500. By puncturing and being inserted through the left lower portion 530 of the intravenous bag 500, the tubular member 100 is positioned to facilitate the distal end 111 of the tubular member's 110 insertion into a proximal end 512 of the intravenous tube 510 and allow the flushing solution housed in the container 100 to flush out the intravenous tube 510. Furthermore, the non-circular portion 350 (see FIG. 1A) of the container 100 is configured to rest flush against the intravenous bag 500 after the tubular member 110 creates an opening and is fully inserted into the intravenous bag 500. Having the non-circular portion 350 rest flush against the intravenous bag allows for the device to be more stably attached and positions the flexible joint 150 and the distal end 111 to more readily insert into the proximal end 512 of the intravenous tube 510 when the amount of liquid remaining 550 in the intravenous bag 500 falls below the threshold.

In the illustrated embodiment the threshold is at the very bottom of the intravenous bag 500. Once the amount of liquid remaining 550 falls to a level below the inserted tubular member 110 the ball float 210 will begin to go down along with the sinking level of the fluid in the intravenous bag 500 and gradually point the distal end 111 downward into the open position. This effectively allows for the flushing solution 125 housed in the container 100 to automatically dispense through the tubular member 110 as soon as the intravenous bag 500 is empty, or the amount of liquid remaining 550 is so little that it can be considered negligible. Once the amount of liquid remaining 550 is zero or negligible the distal end 111 will remain downward in the open position under the weight of the ball float 210.

It is therefore submitted that the instant invention has been shown and described in what is considered to be the most practical and preferred embodiments. It is recognized, however, that departures may be made within the scope of the invention and that obvious modifications will occur to a person skilled in the art. With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. An intravenous bag attachment, comprising:
a container having a tubular member having a first end in fluid communication with an interior volume of the container, the interior volume of the container including a flushing solution;
an outlet disposed on a second end of the tubular member configured to allow the flushing solution housed in the interior volume to exit through the second end of the tubular member;
wherein the tubular member is configured to be inserted into an intravenous bag, wherein the second end of the tubular member is removably connectable to a proximal end of an intravenous tube attached to an opening at a lower end of the intravenous bag;
a ball float disposed within the tubular member, wherein the ball float is configured to float the distal end of the tubular member within a liquid stored in the intravenous bag;
the tubular member further comprising a flexible joint configured to bend to reposition the second end of the tubular member dependent upon an amount of liquid in the intravenous bag;
wherein the ball float is configured to cause the second end of the tubular member to disconnect from the proximal end of the intravenous tube when the amount of liquid in the intravenous bag is above a predefined threshold, and to connect to the proximal end of the intravenous tube when the amount of liquid in the intravenous bag is below the predefined threshold.

2. The intravenous bag attachment of claim 1, wherein the second end of the tubular member tapers to a point and is configured to create an opening in the intravenous bag and to facilitate fluid communication between the intravenous bag and the attachment.

3. The intravenous bag attachment of claim 1, wherein the container is a pouch.

4. The intravenous bag attachment of claim 1, wherein the container is in a shape of a vertical semi-circle having a highest point, a center point, and a lowest point.

5. The intravenous bag attachment of claim 4, wherein the tubular member is disposed along a non-circular portion of the container between the center point and the lowest point, such that the entirety of the flushing solution housed in the internal volume can automatically flow out through the tubular member under the influence of gravity alone.

6. The intravenous bag attachment of claim 4, wherein a non-circular portion of the container is flush against an outer surface of the intravenous bag when the tubular member is fully inserted.

7. The intravenous bag attachment of claim 1, wherein the tubular member is configured to be inserted through a left lower portion of an outer wall of the intravenous bag.

8. The intravenous bag attachment of claim 1, wherein the container and tubular member are both comprised of polyvinyl chloride.

9. The intravenous bag attachment of claim 1, wherein the ball float is comprised of a buoyant, sterile lightweight material that does not disintegrate in a fluid and is an accepted pharmaceutical material.

* * * * *